United States Patent [19]
Puritch et al.

[11] Patent Number: 5,098,467
[45] Date of Patent: Mar. 24, 1992

[54] FATTY ACID BASED HERBICIDAL COMPOSITIONS

[75] Inventors: George S. Puritch, Saanichton; Roderick Bradbury, Sidney; Wenda Mason, Brentwood Bay, all of Canada

[73] Assignee: Safer, Inc., Minneapolis, Minn.

[21] Appl. No.: 710,764

[22] Filed: Jun. 4, 1991

Related U.S. Application Data

[60] Continuation of Ser. No. 588,196, Sep. 26, 1990, which is a division of Ser. No. 421,146, Oct. 13, 1989, Pat. No. 4,975,110.

[51] Int. Cl.$^5$ ............................................. A01N 37/02
[52] U.S. Cl. ................................... 71/113; 71/DIG. 1
[58] Field of Search ............................ 71/113, DIG. 1

[56] References Cited

U.S. PATENT DOCUMENTS

| | | | |
|---|---|---|---|
| 2,626,862 | 1/1953 | Zimmerman et al. | 71/113 |
| 3,645,716 | 2/1972 | Rutkowski | 71/113 |
| 3,932,405 | 1/1976 | Schonbeck et al. | 71/92 |
| 4,313,847 | 2/1982 | Chasin et al. | 252/356 |
| 4,450,001 | 5/1984 | Kaneko et al. | 71/118 |
| 4,631,295 | 12/1986 | Engel et al. | 514/558 |

FOREIGN PATENT DOCUMENTS 49-25131  3/1974  Japan.

OTHER PUBLICATIONS

Puritch, "Pesticidal Soaps and Adjuvants and How Do They Work", Proc. of 23rd Ann. Lower Mainland, Hort. Improvement Assoc. Growers Short Course, Feb. 11, 12, 13 1981, Abbotsford, B.C., pp. 53-67.

Primary Examiner—Richard L. Raymond
Assistant Examiner—B. Bembenick
Attorney, Agent, or Firm—Lahive & Cockfield

[57] ABSTRACT

An environmentally compatible herbicidal composition comprises a fatty acid active ingredient, and a surfactant component. In one embodiment the composition comprises a ready-to-use microemulsion having a fatty acid active ingredient, one or more quaternary ammonium salt surfactant and water. Another embodiment comprises a concentrated herbicidal formulation having a fatty acid active ingredient and one or more surfactants. The concentrate may subsequently be diluted with water to yield a ready-to-use formulation. Each of these compositions is a foliar applied herbicide which effectively controls a variety of unwanted weed and grass species.

The fatty acid component of these herbicidal compositions comprises pelargonic acid which may be used alone or as the predominant component of a mixture of fatty acids including caprylic, pelargonic, capric, undecanoic, and lauric.

9 Claims, No Drawings

FATTY ACID BASED HERBICIDAL COMPOSITIONS

BACKGROUND OF THE INVENTION

The present invention relates to pesticidal compositions having herbicidal activity. More particularly, the invention relates to environmentally compatible herbicides.

The term "pesticide" is used herein in a generic sense and includes insecticides, fungicides, herbicides and miticides. A variety of pesticides are well known and are widely used in agricultural, commercial and household applications. Although useful in controlling insect and mite populations as well as the growth of unwanted flora and fungi, many pesticides have been found to be harmful to the environment as well as to humans, other mammals, birds and fish.

Recently, salts of fatty acids, primarily sodium or potassium fatty acid salts, have been used commercially as pesticides. Compositions having excellent pesticidal properties which exploit these salts are available commercially from Safer, Inc., under the trademark SAFER INSECTICIDAL SOAP. A herbicidally active composition utilizing partially saponified fatty acids as the active ingredient is sold by Safer, Inc. under the trademark SHARPSHOOTER. These fatty acid salts are effective, naturally occurring pesticides which have no known long term environmental effects. Although such fatty acid salts are effective herbicides, it would be desirable to provide an alternative composition having an unsaponified active ingredient while maintaining the environmental compatibility of the pesticide and reducing the eye and skin irritancy of the product.

It is thus an object of this invention to provide an improved, environmentally compatible herbicidal composition. It is also an object to provide more economical and conveniently formulated herbicidal compositions. Another object is to provide an effective herbicidal composition which may be easily formulated in a storage-stable concentrated mixture and which may readily be formed into a usable emulsion by dilution with water. A further object is to provide an effective herbicidally active composition with reduced eye and skin corrosivity. Other objects of the invention will be apparent from the description and claims which follow.

SUMMARY OF THE INVENTION

The present invention features environmentally compatible herbicidal compositions having fatty acid active ingredients. In one embodiment, the herbicidal composition comprises a ready-to-use microemulsion having the fatty acid active ingredient in combination with water and one or more surfactants, preferably in the form of quaternary ammonium salts. In another embodiment, the herbicidal composition comprises a concentrate having a fatty acid active ingredient and one or more anionic and/or nonionic surfactants. This concentrate may be formed into a ready-to-use emulsion upon the addition of a suitable amount of water to dilute the active ingredient to desired concentration levels. The herbicidal compositions of this invention exhibit effective, broad-spectrum herbicidal activity. Moreover, the compositions are contact herbicides which have little or no residual soil activity and are rapidly degraded and used as a nutrient source by soil microorganisms. These compositions are also substantially non-toxic to humans and animals, and, in ready-to-use form, are not corrosive to the eyes and skin.

The fatty acid component of each of the herbicidal composition of the invention comprises one or a mixture of alpha monocarboxylic fatty acids having a hydrocarbon chain with between 8 and 12 carbon atoms. Pelargonic acid is the preferred fatty acid, and it may be used alone or in combination with other fatty acids. Preferably, the fatty acid component is unsaponified.

A ready-to-use herbicidal microemulsion may be prepared by blending together the fatty acid active ingredient, a surfactant component and water. An antifoaming agent may also be included in the formulation to improve processability. The surfactant component comprises at least one, and preferably two, quaternary ammonium salts. Both the fatty acid component and the surfactant component are blended into water at a concentration level approximately equal to that desired in the ready-to-use formulation. That is, the fatty acid component is added at approximately 1 to 8 weight percent and the surfactant component is present at about 2 to 10 weight percent.

The concentrated composition, which forms another embodiment of the invention, comprises a fatty acid component, in an amount ranging from about 40 to 80 weight percent, together with a surfactant component, in an amount ranging from about 20 to 60 weight percent. The surfactant component of this embodiment comprises at least one surfactant selected from the group consisting of ethoxylated phosphate esters, salts of n-alkyl diphenyl ether disulfonates, salts of n-alkyl diphenyl oxide disulfonates, phosphate esters of alkylphenoxy polyoxyethanol, phosphate esters of alkylphenol ethoxylates and mixtures thereof.

The ready-to-use herbicidal microemulsion is, of course, prepared with the proportion of constituents which are desired in the end use product. This composition is storage stable and may be packaged and stored until ready to use.

The concentrated formulation may be stored as a concentrate until ready for use. At such time it is agitated and diluted with water until the concentration of the fatty acid component is in the range of approximately 1 to 8 weight percent.

Unless otherwise noted herein, all percentages refer to percent by weight.

DETAILED DESCRIPTION OF THE INVENTION

The compositions of this invention comprise effective, fatty acid-based herbicides which are environmentally compatible. These compositions are economical, convenient to use and, in ready-to-use form, are non-corrosive to the eyes and skin.

The fatty acid component of each of the herbicidal compositions of this invention comprises one or a mixture of alpha monocarboxylic fatty acids having a hydrocarbon chain with between 8 and 12 carbon atoms. Preferably, the fatty acid is pelargonic acid, which may be used alone or as the major constituent (i.e., about 90%) of a mixture which includes other fatty acids. In one preferred embodiment the fatty acid component comprises a mixture of pelargonic acid, caprylic and capric acids wherein pelargonic acid accounts for most of the mixture and caprylic and capric acids are present in relatively small amounts. Such a mixture, having about 94% pelargonic acid, 4% caprylic acid and 2% capric acid, is commercially available under the trademark "EMERY 1202" from Emery Division, Quantum Chemical Corporation, Cincinnati, Ohio. In another embodiment, pelargonic acid may be combined with undecanoic acid and utilized as the active ingredient of the herbicidal composition. Preferably, the active ingredient is an unsaponified single fatty acid or a mixture of unsaponified fatty acids.

The fatty acid components set forth above are merely examples of currently preferred fatty acids and fatty acid mixtures. It is expected that the ratios of the various constituents of these fatty acids and mixtures may be altered, or that other combinations of fatty acid having between 8 and 12 carbon atoms may be used, to obtain the same or better results.

In one embodiment of the invention a ready-to-use herbicidal formulation is prepared as a storage-stable microemulsion having a fatty acid active ingredient, a surfactant component and water. The fatty acid active ingredient comprises approximately 1 to 8 weight percent, and most preferably about 5 weight percent of the formulation. The surfactant component comprises approximately 2 to 10 weight percent, and most preferably about 5 weight percent of the formulation.

The surfactant component of ready-to-use microemulsion comprises one or more surfactants such as quaternary ammonium salts, ethoxylated phosphate esters, polyoxyethylene derivatives of fatty acid partial esters of sorbitol anhydrides, castor oil ethoxylate, isopropyl alcohol and mixtures thereof. In a preferred embodiment, the surfactant component comprises a quaternary ammonium salt and most preferably a mixture of two such salts. Examples of preferred quaternary ammonium salts are methyloctadecyl POE (15) ammonium chloride and trimethyl allow ammonium chloride. Preferred quaternary ammonium salt compounds are sold commercially under the trademarks "Ethoquad 0/25", "Ethoquad 18/25" and "Arquad T50" by Akzo America, Inc. of Chicago, Ill. Currently, a combination of "Ethoquad 18/25" and "Arquad T50" form the most preferred surfactant component.

Preferably, the ready-to-use herbicidal microemulsion also also includes a small amount (i.e., about 0.05%) anti-foaming agent as a processing aid. While virtually any anti-foaming agent will suffice, the preferred agents are those which are environmentally compatible. One currently preferred anti-foaming agent is a silicone defoamer sold under the designation "FG-10 Antifoam Emulsion" by Dow Corning of Midland, Mich.

Examples of various preferred herbicidal microemulsion formulations are shown below in Table I. This table identifies ready-to-use herbicidal microemulsions having a fatty acid concentration of approximately 5 weight percent. The most preferred formulation is that labelled in Table I as formulation F. One having ordinary skill in the art may easily prepare alternative microemulsions with equal or better efficacy simply by varying the concentration of fatty acid and surfactant, or by substituting other fatty acid or surfactant compositions.

TABLE I

| | Fatty Acid* | Surfactant 1 | Surfactant 2 | Water** |
|---|---|---|---|---|
| A | 5% | Ethoquad 0/25 (5%) | Isopropyl alcohol (9.9%) | 80.1% |
| B | 5% | Ethoquad 0/25 (5%) | — | 90% |
| C | 5% | Tween 80 (4.5%) | Trylox CO-40 (0.5%) | 90% |
| D | 5% | Ethoquad 0/25 (4.5%) | Stepfac 8170 (0.5%) | 90% |
| E | 5% | Ethoquad 18/25 (5%) | — | 90% |
| F | 5% | Ethoquad 18/25 (4.5%) | Arquad T50 (0.5%) | 90% |

*The fatty acid component comprises about 94% pelargonic acid, 2% capric acid and 4% caprylic acid.
**In each formulation, the amount of water may be reduced to accommodate the addition of an anti-foaming agent.

Many combinations of fatty acid component, oil component and emulsifier component may be used to obtain a herbicidal microemulsion having effective phytotoxicity. A ready-to-use herbicidal emulsion according to this invention may include about 1-8 wt % fatty acid, 2-10% surfactant and the balance water. Most preferably the herbicidal concentrate comprises 5% fatty acid, 5% surfactant, a minor amount (i.e., 0.05%) of antifoaming agent and a balance of water.

The invention also features, in another embodiment, a concentrated fatty acid-based herbicidal composition having a fatty acid active ingredient and one or more hydrophobic surfactants. Typically, the concentrate contains from about 40 to 80 weight percent fatty acid and about 20 to 60 weight percent surfactant(s). In a preferred embodiment, the fatty acid comprises about 80 weight percent of the concentrated formulation while the remainder comprises one or more surfactants. The concentrate is a storage-stable formulation which is diluted with water and agitated before use to yield a ready-to-use formulation having approximately 1 to 8 weight percent fatty acid and approximately 0.25 to 2.0 weight percent surfactant component.

The fatty acid component of this embodiment is, as noted above, substantially the same as that used to prepare the ready-to-use microemulsion. The surfactant component may, however, be somewhat different from that used with microemulsion. Preferably, the surfactant comprises one or more surfactants. The most preferred surfactants are those which lack a terminal group, such as a hydroxyl group, which is reactive with the fatty acid component. The most preferred surfactants for use with this composition are those which have sulfate, phosphate and carbonate terminal groups, which do not react with the fatty acid component. Among such preferred surfactants are ethoxylated phosphate esters (such as phosphate esters of alkylphenoxy polyethoxyethanol and phosphate esters of alkylphenol ethoxylates), salts of n-alkyl diphenyl ether disulfonates, salts of n-alkyl diphenyl oxide disulfonates, polyalkylene derivatives of propylene glycol and castor oil ethoxylates. Such compounds are available under various tradenames from a number of manufacturers. Preferred, commercially available ethoxylated phosphate ester surfactants include "Stepfac 8170" available from Stepan Co. of Northfield, Ill. and "Emphos" available from Witco Chemicals of Brooklyn, N.Y. Also, the salts of n-alkyl diphenyl oxide disulfonates are commercially available under the trademark "Dowfax 3B2" from Dow Chemicals of Midland, Mich. The salts of n-alkyl diphenyl ether disulfonates are available under the trademark "Fenopon C0436" from GAF Corp. of New York, N.Y. The polyalkylene derivatives of propylene glycol are available under the trademark "Pluronic F68" from BASF of Parsippany, N.J. The castor oil ethoxylates are available from GAF Corp. of New York, N.Y. under the trademark "Mulgofen".

Table II, shown below, illustrates various preferred combinations of fatty acids and surfactants which may be used to prepare the concentrated herbicide of this invention. The most preferred is formulation G which, in addition to the fatty acid, includes about 18 percent Stepfac 8170 (phosphate ester of alkyl phenoxy polyethoxyethanol) and about 2 percent Dowfax 3B2 (sodium salt of alkyldiphenyl oxide sulfate). It is believed that the Dowfax surfactant improves the composition by helping to stabilize the composition by preventing the creaming which often results when only an ethoxylated phosphate ester is used as the surfactant. Another useful, albeit somewhat less stable, formulation is Formulation C of Table II which includes only an ethoxylated phosphate ester (either Stepfac or Emphos) as a surfactant.

TABLE II

| | Fatty Acid* | Surfactant 1 | Surfactant 2 |
|---|---|---|---|
| A | 80% | 18% Tween 80 | 2% Mulgofen EL719 |
| B | 80 | 20% Fenopon C0436 | — |
| C | 80 | 20% Stepfac 8170 | — |
| D | 80 | 20% Aerosol OT-75 | — |
| E | 80 | 10% Dowfax 3B2 | 10% Aerosol OT-75 |
| F | 80 | 10% Dowfax 3B2 | 10% Stepfac 8170 |
| G | 80 | 2% Dowfax 3B2 | 18% Stepfac 8170 |
| H | 80 | 2% Pluronic F68 | 18% Stepfac 8170 |

*The fatty acid component comprises approximately 94% pelargenic acid, 2% capric acid and 4% caprylic acid.

The formulations set forth in Table II are provided only as examples of preferred herbicidal concentrates. As noted above, Formulation G is currently the preferred formulation. However, it is understood that one having ordinary skill in the art may easily substitute equivalent or different surfactants, used in the same or different concentrations, as those of Table II to achieve acceptable herbicidal activity. Also, other fatty acids and mixtures of fatty acid having between 8 and 12 carbon atoms may be substituted for the fatty acid composition of Table II to achieve equivalent or superior efficacy.

A concentrate may also be prepared in a solid from which, when desired, may be dissolved in water to yield a ready-to-use herbicidal formulation which may be used to control weeds.

The present herbicidal compositions may be prepared through a variety of formulation and mixing techniques well known to those having ordinary skill in the art. One preferred technique for formulating the herbicidal microemulsion involves charging a stainless steel or high density polyethylene tank, equipped with a paddle strirrer, with the batch quantity of water at a temperature range of between 15°-30° C., and commencing agitation under low to medium shear conditions. The batch quantity of the surfactant component, followed by the anti-foaming agent, is then added while commencing vigorous agitation for about one hour. It may be necessary to mix under high shear conditions in order to dissolve some quaternary ammonium salts. Next, the batch quantity of the fatty acid component is added while continuing agitation for an additional 30 minutes. This process yields a storage-stable, ready-to-use, herbicidal microemulsion.

The concentrated herbicidal composition of this invention may be prepared by charging a stainless steel or high density polyethylene tank (having a paddle stirrer) with a batch quantity of the fatty acid component, and commencing agitation. Next, a batch quantity of one surfactant (e.g., ethoxylated phosphate ester) may be added, followed by the batch quantity of a second surfactant (e.g., an n-alkyl diphenyl oxide disulfonate). After the addition of the surfactant component agitation continues for approximately 30 minutes. This procedure yields a storage-stable, concentrated herbicidal composition which may be diluted with water prior to use.

The present formulations are foliar applied, non-selective herbicides which may be sprayed upon unwanted weeds and grasses. In one embodiment a ready-to-use formulation is provided. In another embodiment, a concentrated formulation is provided which may later be diluted in water to achieve a ready-to-use formulation having an active ingredient concentration in the range of approximately 1-8% fatty acid active ingredient. Most preferably, the concentration of active ingredient is in the range of 3-5%.

Each of the herbicidal compositions of this invention are effective, environmentally compatible herbicides. The microemulsion is best suited for household and gardening applications by consumers due to its convenience, its eye and skin non-corrosivity and its relatively low eye and skin irritancy. The concentrate is best suited for commercial and agricultural application due to its economy and its favorable dilution factor.

The herbicidal formulations in ready-to-use form, may be applied directly to the unwanted weeds and grasses. These compositions are most effective against young, succulent and actively growing weeds less than five inches in height. Several applications of the compositions may be necessary to control certain grasses and established weeds. Maturing (flowering) and woody weeds are less susceptible to the formulation. Repeated applications of the composition may be necessary to kill perennial weeds.

Examples of annual weeds controllable by these herbicidal compositions include Lambsquarter, Pigweed, Mustard, Shepherd's purse, Spiney annual sowthistle, Pineapple weed, Scentless mayweed, Wild buckwheat, Green foxtail, Stinkweed, Corn spurry, Common groundsel, Red sheep sorrel, Common chickweed, Wild radish, Common purslane, Whitestem filaree, Little mallow, Volunteer oat, False flax and Barnyard grass.

Examples of perennial weeds controllable by these herbicides include Spotted catsear, True dandelion, Narrow-leaf plantation, Curled dock, Horsetail, Mouse-eared chickweed, Lupine, Clovers, Perennial ryegrass, Thistles and Quackgrass.

The herbicidal formulations of this invention may be applied by conventional spraying means. The formulation is most effective when applied to thoroughly cover all the plant foliage. Preferably, the composition is sprayed in a carrier, such as water, where the carrier is applied at the rate of approximately 10 to 200 gallons per acre and most preferably 60 to 150 gallons per acre.

The following non-limiting examples serve to further describe the invention.

EXAMPLE I

A herbicidal composition corresponding to Formulation F of Table I was prepared. The formulation was applied, in various quantities, to the weed species shown below in Table III using a hand-held trigger sprayer. Plant mortality was assessed 5 days after spraying using the method described in Little, T. M. et al., *Statistical Methods in Agricultural Research*, J. Wiley and Sons (1975).

TABLE III

| Trt No. | Weed Species | Volume Applied (X ml) | Ground Cover | Growth Stage[2] | Mortality % |
|---|---|---|---|---|---|
| 1 | Corn Spurry | 67.1 | 3-60 | V-F-SE | 16 |
| 2 |  | 299 | 15-65 | V-F-SE | 93 |
| 3 |  | 138 | 10-40 | V-F-SE | 65 |
| 4 |  | 120 | 5-60 | V-F-SE | 64 |
| 1 | Wild Mustard | 67.1 | 5-20 | V-F | 5 |
| 2 |  | 299 | 5-30 | V-F | 78 |
| 3 |  | 138 | 10-25 | F-SE | 12 |
| 4 |  | 120 | 10-30 | F | 30 |
| 1 | Lambsquarter | 67.1 | 2-50 | V-F-SE | 10 |
| 2 |  | 299 | 15-40 | V-SE | 78 |
| 3 |  | 138 | 2-30 | V-F | 53 |
| 4 |  | 120 | 2-40 | V-F-SE | 19 |
| 1 | Red root | 67.1 | — | — | — |
| 2 | pigweed[1] | 299 | — | — | — |
| 3 |  | 138 | 2-3 | V | 100 |
| 4 |  | 120 | 2-5 | V | 100 |
| 1 | Narrow leaf | 67.1 | 2-5 | V | 50 |
| 2 | plantain | 299 | 1-5 | V | 100 |
| 3 |  | 138 | 2 | R-V | 50 |
| 4 |  | 120 | 1-2 | V | 0 |
| 1 | Green foxtail | 67.1 | 2-30 | V-SE | 0 |
| 2 |  | 299 | 1-20 | V-SE | 55 |
| 3 |  | 138 | 1-5 | V-SE | 0 |
| 4 |  | 120 | 5 | F-SE | 0 |
| 1 | Shepherd's | 67.1 | 2-5 | V | 75 |
| 2 | purse | 299 | 3-5 | V | 100 |
| 3 |  | 138 | — | — | — |
| 4 |  | 120 | — | — | — |

[1]Species did not occur in sufficient quantity to permit inclusion
[2]V = vegatative; R = rosette; F = flowering; SE = seeding

EXAMPLE II

A concentrate of herbicidal formulation G of Table II was prepared. The formulation was diluted with water to concentrations of 2 gallons per acre (gpa) fatty acid active ingredient (ai), 4 gpa fatty acid ai and 6 gpa ai. The compositions were applied in an orchard to the weeds shown in Table IV using a back pack sprayer timed to deliver 60, 90 and 120 gpa aqueous carrier for each concentration level of the formulation. Paraquat and glyphosate were each applied at 0.375 gpa ai with 60 gpa aqueous carrier by way of comparison.

TABLE IV

| Weed Common Name | Size Range (Inches) | Growth Stage[2] | Occurance (Range %) |
|---|---|---|---|
| False dandelion | 1-14 D[1] | V/F | 0-25 |
| Grasses | 4-20 | V/Se | <5-60 |
| Cranesbill | 2-14 D | V/F | 0-20 |
| Narrow-leaf plaintain | 3-20 D | V/F | 0-5 |
| Common groundsel | 2-22 | V/Se | 0-10 |
| Annual sowthistle | 1-12 D | V | 0-10 |
| Purple vetch | 4-24 D | V/F | 0-<5 |
| Black medic | 1-14 D | V/F | 0-5 |
| Sheep sorrel | 1-16 | V/Se | 0-5 |
| Purple dragon-head | 2-20 | V | 0-10 |
| Mouse-eared chickweed | 4-14 | F/Se | 0-5 |
| English daisy | 3-8 | F | 0-30 |
| Wild carrot | 5-20 D | V/F | 0-25 |
| Bedstraw | 2-14 D | V/F | 0-20 |
| Dandelion | 2-18 D | V/Se | 0-10 |
| Hawksbeard | 1-20 | V/F | 0-10 |
| Clover | 1-2 | V | 0-15 |

[1]D = plant diameter
[2]V = vegetative; F = flowering; Se = seeding

The plots, 2.5 m by 7.5 m in size, were arranged in a randomized complete block design. The percent weed control for each concentration of active ingredient was estimated using the method described in Little, T. M. et al., *Statistical Methods in Agricultural Research*, J. Wiley and Sons (1975). Tables V and V(A) illustrate the observed weed control for a first spray with an assessment made 14 days after treatment. Tables VI and VI(A) illustrate a second spray (made 35 days after the first treatment) with assessment made 14 days after treatment.

TABLE V

| Common Name[1] | Percent Weed Damage (14 D.A.T.) | | | | | | | | |
|---|---|---|---|---|---|---|---|---|---|
|  | 2 gpa ai | | | 4 gpa ai | | | 6 gpa ai | | |
|  | 60 | 90 | 120 | 60 | 90 | 120 | 60 | 90 | 120 |
|  | gpa carrier | | | gpa carrier | | | gpa carrier | | |
| False dandelion | 61 | 79 | 85 | 94 | 88 | 94 | 96 | 92 | 98 |
| Grasses | 46 | 42 | 30 | 61 | 65 | 69 | 79 | 88 | 92 |
| Cranesbill | 24 | 46 | 24 | 61 | 65 | 79 | 82 | 76 | 85 |
| Narrow-leaf plantain | 14 | 65 | 97 | 75 | 90 | — | 42 | 87 | — |
| Common groundsel | 100 | 100 | 98 | 100 | 100 | 100 | 100 | 100 | 100 |
| Annual sowthistle | 97 | 97 | — | 99 | 100 | 72 | — | 100 | 100 |
| Purple vetch | 44 | 95 | 50 | 99 | — | 97 | 97 | 100 | 97 |
| Black medic | 72 | 70 | — | 97 | — | — | — | 100 | 99 |
| Sheep sorrel | 34 | 97 | 75 | 50 | 90 | 99 | 99 | 97 | 98 |
| Purple dragon head | 99 | — | 83 | 79 | 90 | 97 | 98 | 99 | 98 |
| Mouse-eared chickweed | 99 | 100 | 100 | 100 | 100 | 100 | — | — | 99 |
| English daisy | 42 | 50 | 46 | 57 | 29 | 60 | 79 | 61 | 61 |
| Wild carrot | 72 | 72 | — | — | 94 | — | 85 | 93 | — |
| Bedstraw | 60 | — | 94 | 94 | — | 90 | 97 | 98 | — |
| Dandelion | 76 | 65 | 82 | 85 | 72 | 95 | 88 | 93 | 90 |

[1]Other weeds include Clover, Mallow, Blackberry, Canada thistle, Stork's bill, Henbit, Prickly lettuce, Chickweed, Oregon grape, Shepherd's purse.

TABLE V(A)

| | Percent Weed Damage (14 D.A.T.) | |
|---|---|---|
| Common Name[1] | Parraquat .375 gpa ai 60 gpa carrier | Glyphosate .375 gpa ai 60 gpa carrier |
| False dandelion | 69 | 61 |
| Grasses | 82 | 72 |
| Cranesbill | 79 | 27 |
| Narrow-leaf plantain | — | 42 |
| Common groundsel | 98 | 82 |
| Annual sowthistle | 100 | 79 |
| Purple vetch | 87 | 34 |
| Black medic | 90 | 14 |
| Sheep sorrel | 99 | 79 |
| Purple dragon-head | 87 | — |
| Mouse-eared chickweed | — | 72 |
| English daisy | 83 | 5 |
| Wild carrot | 94 | — |
| Bedstraw | 85 | 75 |
| Dandelion | 79 | 50 |

[1]Other weeds include Clover, Mallow, Blackberry, Canada thistle, Stork's bill, Henbit, Prickly lettuce, Chickweed, Oregon grape, Shepherd's purse.

TABLE VI

| | Percent Weed Damage After Respray In Orchard (14 D.A.T.) | | | | | | | | |
|---|---|---|---|---|---|---|---|---|---|
| | 2 gpa ai | | | 4 gpa ai | | | 6 gpa ai | | |
| Common Name[1] | 60 gpa carrier | 90 gpa carrier | 120 gpa carrier | 60 gpa carrier | 90 gpa carrier | 120 gpa carrier | 60 gpa carrier | 90 gpa carrier | 120 gpa carrier |
| False dandelion | 70 | 79 | 72 | 70 | 72 | 72 | 79 | 92 | 90 |
| Grasses | 88 | 88 | 90 | 90 | 79 | 96 | 96 | 92 | 92 |
| Cranesbill | 75 | 94 | 82 | 83 | 97 | 79 | 85 | 75 | 97 |
| Sheep sorrel | 39 | — | — | — | 97 | 34 | 34 | — | — |
| English daisy | 65 | 85 | 50 | 50 | 79 | 85 | 79 | 90 | 65 |
| Wild carrot | 57 | — | 85 | 65 | 97 | 93 | — | 90 | 65 |
| Dandelion | — | 97 | 79 | — | 97 | 90 | 90 | 79 | 97 |
| Hawksbeard | 20 | 65 | 9 | 42 | 34 | 65 | 57 | 65 | 79 |
| Clover | 50 | — | 65 | 65 | 79 | 79 | 79 | 79 | — |

[1]Other weeds include Narrow-leaf plantain, Common groundsel, Annual sowthistle, Purple vetch, Black medic, Purple dragon-head, Mouse-eared chickweed, Bedstraw.

TABLE VI(A)

| | Percent Weed Damage After Respray In Orchard (14 D.A.T.) | |
|---|---|---|
| Common Name[1] | Parraquat .375 gpa ai 60 gpa carrier | Glyphosate .375 gpa ai 60 gpa carrier |
| False dandelion | 97 | 97 |
| Grasses | 95 | 97 |
| Cranesbill | — | 90 |
| Sheep sorrell | — | 50 |
| English daisy | — | 97 |
| Wild carrot | — | 50 |
| Dandelion | — | 34 |
| Hawksbeard | 34 | — |
| Clover | — | 50 |

[1]Other weeds include Narrow-leaf plantain, Common groundsel, Annual sowthistle, Purple vetch, Black medic, Purple dragon-head, Mouse-eared chickweed, Bedstraw.

What is claimed is:

1. A method for controlling the growth of unwanted vegetation, comprising the steps of:
   providing a herbicidal composition, in the form of a microemulsion, consisting essentially of approximately 1 to 8 percent by weight of a herbicidally effective amount of a saturated linear, monocarboxylic fatty acid selected from the group consisting of the acids caprylic, palargonic, capric, undecanoic, lauric, and mixtures thereof; approximately 2 to 10 percent by weight of a surfactant component; and a balance of a carrier; and
   applying the herbicidal composition to unwanted vegetation in an amount ranging between about 10 to 200 gallons of carrier per acre.

2. The method of claim 1 wherein the carrier is water.

3. The method of claim 2 wherein the fatty acid component of the herbicidal composition is present at a range of about 3 to 5 percent by weight.

4. The method of claim 1 wherein the fatty acid component of the herbicidal composition is predominantly pelargonic acid.

5. The method of claim 4 wherein the fatty acid component of the herbicidal composition comprises approximately 94 weight pelargonic acid, 4 weight percent caprylic acid, and 2 weight percent capric acid.

6. The method of claim 1 wherein the surfactant component of the herbicidal composition comprises at least one quaternary ammonium salt.

7. The method of claim 6 wherein the surfactant component of the herbicidal composition comprises two quaternary ammonium salts.

8. The method of claim 7 wherein one surfactant is an alkyl trimethylammonium chloride.

9. The method of claim 7 wherein one surfactant is a polyethoxylated quaternary ammonium chloride.

* * * * *